US00PP10185P

United States Patent [19]

Wiles

[11] Patent Number: Plant 10,185

[45] Date of Patent: Jan. 6, 1998

[54] VARIETY OF GERANIUM NAMED LOUISE

[75] Inventor: Linda S. Wiles, Scottdale, Pa.

[73] Assignee: Oglevee, Ltd., Connellsville, Pa.

[21] Appl. No.: 682,109

[22] Filed: Jul. 17, 1996

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Webb Ziesenheim Bruening Logsdon Orkin & Hanson, P.C.

[57] ABSTRACT

A new and distinct variety of ivy geranium that has a long trailing habit, a strong zone and a soft medium salmon pink appearance against a medium green foliage.

1 Drawing Sheet

BACKGROUND OF THE NEW PLANT

The present invention comprises a new and distinct cultivar of *Pelargonium×peltatum* known by the varietal name "Louise". The new variety was discovered in a selective breeding program at Oglevee, Ltd. by Linda S. Wiles. The new variety is a selection from a seedling cross from Nanette, the seed parent,×Nicole, the pollen parent, (U.S. Plant Pat. Nos. 7,360 and 7,358, respectively).

The new cultivar was discovered in 1993 at 152 Oglevee Lane, Connellsville, Pa., was first asexually reproduced by cuttings on Jan. 25, 1994 at Connellsville, Pa. It has been found to retain its distinct characteristics through successive propagations.

The new cultivar has long trailing habit similar to the variety Nanette. The new cultivar's color is not similar to either parent and its habit is longer than the variety Nicole.

The new cultivar, when grown in a glass greenhouse in Connellsville, Pa., using full light, 60° F. night temperature, 68° F. day temperature, and grown in a soilless media with constant fertilizer of 200–250 parts per million nitrogen and potassium, has a response time from a rooted cutting to a flowering plant in 10 cm. pot of six weeks.

DESCRIPTION OF THE DRAWING

The accompanying drawing illustrates a new cultivar, the color being as true as possible with color illustrations of this type.

DESCRIPTION OF THE NEW PLANT

The following detailed descriptions set forth the characteristics of the new cultivar. The data which define these characteristics were collected from asexual reproductions carried out by Oglevee Ltd. in Connellsville, Pa. The plants were started as rooted cuttings which were potted and then flowered six weeks later. The plant histories were taken of plants blossomed under full light in a greenhouse and color readings were taken indoors under 200–220 foot candles of cool white fluorescent light. Color references are primarily to The R.H.S. Colour Chart of The Royal Horticultural Society of London.

The Plant

Classification:

*Botanical.*—*Pelargonium×peltatum.*

*Commercial.*—Ivy geranium named "Louise".

Height: 26 to 28 cm. above media surface.

Growth: Cascading mound.

Foliage: Slightly reflective, slightly pubescent; stalked leaf attachment.

Leaves:

*Size.*—8 to 11.5 cm.

*Shape.*—Reniform, cordate base, zig-zag undulation.

*Margin.*—Pedately lobed.

*Texture.*—Leathery, smooth.

*Color.*—Top: Green Group 137A; Bottom: Green Group 137D; Zone: Brown Group 200A.

*Ribs and veins.*—Venation: Palmate. Color: Yellow-Green Group 146C.

Petioles:

*Length.*—5.5 to 8 cm.

*Color.*—Yellow-Green Group 146C.

Stem:

*Color.*—Yellow-Green Group 146C.

*Internodes.*—4.5 to 6 cm. in length.

The Bud Cluster

Shape: Elliptical cluster.

Size: 4 to 5 cm.

Inflorescence

Blooming Habit: Free, early and continuous flowering.

Borne: Florets on pedicel, pedicel on peduncle 6.5 to 9 cm. above foliage.

Closed florets:

*Bud size.*—Just showing color at 9 mm. wide and 1.9 cm. long.

Size: Fully Open Bloom: 10.5 to 13 cm.

Open florets:

*Form.*—Semi-double; open to slightly cupped; irregularity caused by petaloids.

*Color.*—Top: Red Group 52C with Red Group 52B veins. Overall Petal Color: Red Group 52C. Bottom: Red Group 48D. Eye: Upper three petals are Red Group 52C with Red Group 53A and Red Group 49D veins.

Petals: 13 in number; petal arrangement gives the floret a frilly appearance.

Size: 5.3 to 5.8 cm. across.

Texture and appearance: Satiny; appearance from a distance is a soft salmon pink above medium green foliage.

Petaloids:

*Quantity.*—8.

*Shape.*—Irregular, tubular, twisted, partial petal types.

*Color.*—Top: Red Group 52C; Bottom: Red Group 49A with light veining at Red Group 49D.

Pedicel:
*Length.*—3 to 4 cm.
*Color.*—Yellow-Green Group 146C.
Peduncle:
*Length.*—18 to 22 cm.
*Color.*—Yellow-Green Group 146C.
Disease resistance: Not known.
Lasting quality: Less prone to shattering.

Reproductive Organs

Stamens:
*Anthers.*—2.5 to 3 mm. in length.
*Filaments.*—0.4 to 0.9 cm. in length, white blushed with petal color.
*Pollen.*—Golden Yellow.
Pistils:
*Number.*—1 per floret.
*Stigma.*—5 lobed.
*Length.*—0.8 to 0.9 cm.
*Stigma.*—Red-Purple in color.
*Style.*—5 cm. in length.
*Ovaries.*—Color: Green, pubescent; superior. Length: 6 mm.
Fruit: None observed.

General Characteristics

A new geranium that is a long trailing ivy geranium similar to Salmon Queen. Large Florets, a strong zone, rooting ease and speedy finishing time are all improvements over Salmon Queen.

I claim:

1. A new and distinct variety of ivy geranium plant as shown herein and characterized by a long trailing habit, a strong zone and a soft salmon pink appearance above medium green foliage.

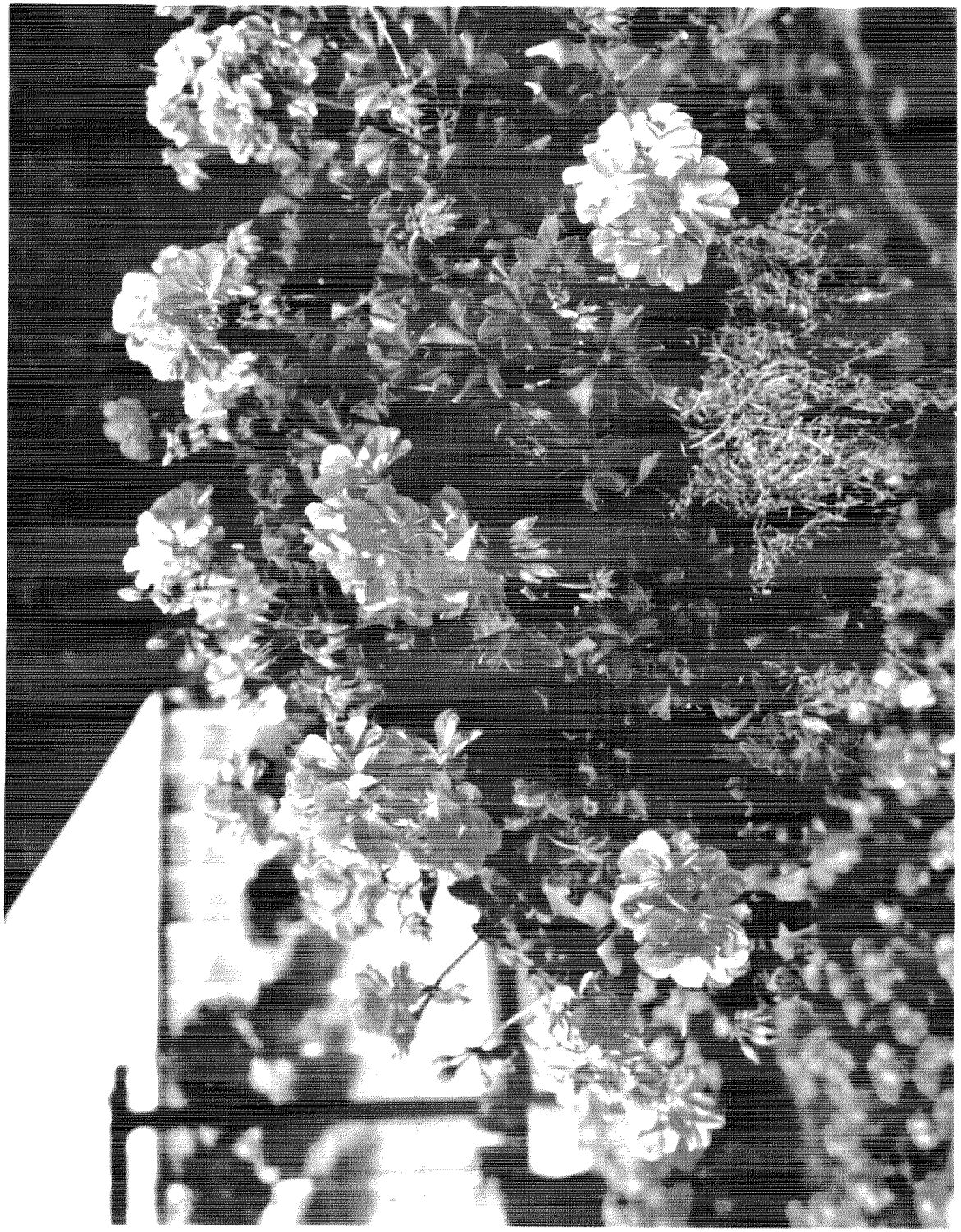

* * * * *